United States Patent [19]

O'Neil et al.

[11] Patent Number: 4,791,206

[45] Date of Patent: Dec. 13, 1988

[54] TRIAZOLE-ORGANODITHIOPHOSPHATE REACTION PRODUCT ADDITIVES FOR FUNCTIONAL FLUIDS

[75] Inventors: Robert M. O'Neil, Boothstown, England; Ulrich Kristen; Ulrich Häring, both of Riehen, Switzerland

[73] Assignee: Ciba-Geigy Corporation, Ardsley, N.Y.

[21] Appl. No.: 861,186

[22] Filed: May 9, 1986

[30] Foreign Application Priority Data

May 16, 1985 [GB] United Kingdom ................ 8512444
Jun. 19, 1985 [GB] United Kingdom ................ 8515477

[51] Int. Cl.$^4$ ............................................. C07F 9/65
[52] U.S. Cl. .................................... 548/108; 548/101; 548/112; 548/113; 548/118; 548/257; 548/260; 548/262; 548/269; 546/22; 544/132; 540/542
[58] Field of Search ............... 548/101, 108, 257, 260, 548/262, 269, 112, 113, 114, 118; 544/132; 546/22; 540/542

[56] References Cited

U.S. PATENT DOCUMENTS 4,456,539 6/1984 Shim ................................. 252/46.7
4,701,273 10/1987 Brady et al. ...................... 252/32.5

FOREIGN PATENT DOCUMENTS 2156813 10/1985 United Kingdom .

Primary Examiner—Richard L. Raymond
Attorney, Agent, or Firm—Luther A. R. Hall; Harry Falber

[57] ABSTRACT

New reaction products, useful as additives for functional fluids, are obtained by reacting, at elevated temperature,
(A) a triazole having the formula IA or IB:

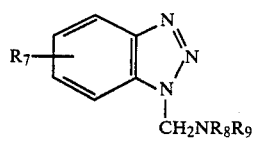

IA

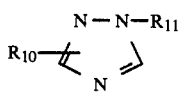

IB wherein
$R_7$ is hydrogen or a $C_1$-$C_{20}$ alkyl residue;
$R_8$ and $R_9$ are the same or different and each is $C_1$-$C_{20}$ alkyl, $C_3$-$C_{20}$ alkenyl, $C_5$-$C_{12}$ cycloalkyl, $C_7$-$C_{13}$ aralkyl, $C_6$-$C_{10}$ aryl or $R_8$ and $R_9$, together with the nitrogen atom to which they are attached, form a 5-, 6- or 7-membered heterocyclic residue or $R_8$ and $R_9$ is each a residue of formula:

$$R_{12}X[(\text{alkylene})O]_n(\text{alkylene})— \qquad II$$

wherein X is O, S or $N(R_{12})$, $R_{12}$ is hydrogen or $C_1$-$C_{20}$ alkyl, "alkylene" is a $C_1$-$C_{12}$ alkylene residue and n is 0 or an integer from 1 to 6;
$R_{10}$ is hydrogen, $C_1$-$C_{20}$ alkyl or $C_6$-$C_{10}$ aryl or $C_7$-$C_{18}$ alkyl phenyl; and $R_{11}$ is hydrogen, $C_1$-$C_{20}$ alkyl or a residue —$CH_2NR_8R_9$ wherein $R_8$ and $R_9$ have their previous significance; with
(B) an organodithiophosphate having the formula:

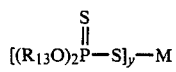

III in which $R_{13}$ is a $C_1$-$C_{20}$ alkyl or $C_7$-$C_{18}$ alkyl phenyl or $C_7$-$C_{13}$ aralkyl group, M is a metal ion of Group IA, IB, IIA, IIB, VB, VIB, VIIB or VIII of the Periodic System of Elements, and y is the valency of M.

12 Claims, No Drawings

TRIAZOLE-ORGANODITHIOPHOSPHATE REACTION PRODUCT ADDITIVES FOR FUNCTIONAL FLUIDS

The present invention relates to new reaction products and to their use in improving the properties of functional fluids.

In a pending patent application GB No. 2156813, we have described new N-substituted compounds, useful as metal deactivators in functional fluids, and having the formula:

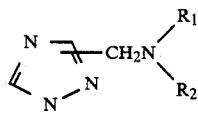

in which $R_1$ and $R_2$ are the same or different and each is $C_1$-$C_{20}$ alkyl, $C_3$-$C_{20}$ alkenyl, $C_5$-$C_{12}$ cycloalkyl, $C_7$-$C_{13}$ aralkyl, $C_6$-$C_{10}$ aryl, or $R_1$ and $R_2$, together with the nitrogen atom to which they are each attached may form a 5-, 6- or 7-membered heterocyclic residue, or $R_1$ and $R_2$ is each a residue of formula:

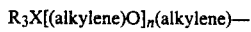

$$R_3X[(alkylene)O]_n(alkylene)-$$

in which X is O, S or $N(R_3)$, $R_3$ is hydrogen or $C_1$-$C_{20}$ alkyl, "alkylene" is a $C_1$-$C_{12}$ alkylene residue and n is O or an integer from 1 to 6, or $R_1$ has its previous significance and $R_2$ is a residue of formula:

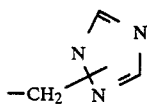

or $R_2$ is a residue of formula:

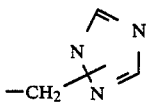

and $R_1$ is a residue of formula:

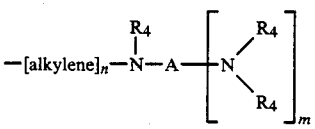

wherein, m is zero or 1 and, when m is zero, A is a residue of formula:

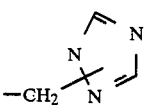

and, when m is 1,

A is alkylene or $C_6$-$C_{10}$ arylene and alkylene and n are as defined above and $R_4$ is a residue of formula:

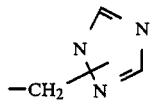

Moreover, in U.S. Pat. No. 4,456,539, there are described the reaction products of:
(a) alkylbenzotriazoles having the formula:

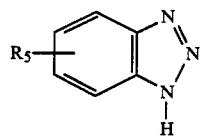

wherein $R_5$ is 1-12C alkyl; and
(b) organodithiophosphates having the formula:

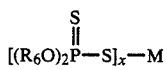

$$[(R_6O)_2P-S]_x-M$$

in which $R_6$ is the same or different hydrocarbyl group, preferably a 1-25C alkyl or alkaryl group, M is a cation including an ammonium ion or a metal, preferably from Groups IA, IIA, IIB, VIB and VII. The reaction products are said to be useful as antioxidants in lubricant compositions.

We have now found certain new reaction products of triazoles and organodithiophosphates which have excellent metal passivating and antioxidant properties in functional fluids, and which have increased solubility in functional fluids relative to the un-reacted triazoles.

Accordingly, the present invention provides a new reaction product which has been obtained by reacting, at elevated temperature,
(A) a triazole having the formula IA or IB:

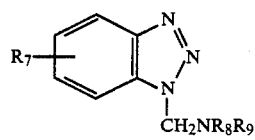

IA

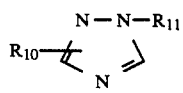

IB wherein
$R_7$ is hydrogen or a $C_1$-$C_{20}$ alkyl residue;
$R_8$ and $R_9$ are the same or different and each is $C_1$-$C_{20}$ alkyl, $C_3$-$C_{20}$ alkenyl, $C_5$-$C_{12}$ cycloalkyl, $C_7$-$C_{13}$ aralkyl, $C_6$-$C_{10}$ aryl or $R_8$ and $R_9$, together with the nitrogen atom to which they are attached, form a 5-, 6- or 7-membered heterocyclic residue or $R_8$ and $R_9$ is each a residue of formula:

$$R_{12}X[(alkylene)O]_n(alkylene)-$$   II wherein
X is O, S or $N(R_{12})$, $R_{12}$ is hydrogen or $C_1$-$C_{20}$ alkyl, "alkylene" is a $C_1$-$C_{12}$ alkylene residue and n is O or an integer from 1 to 6;

$R_{10}$ is hydrogen, $C_1$-$C_{20}$ alkyl or $C_6$-$C_{10}$ aryl or $C_7$-$C_{18}$, preferably $C_7$-$C_{13}$ alkyl phenyl; and $R_{11}$ is hydrogen, $C_1$-$C_{20}$ alkyl or a residue —$CH_2NR_8R_9$ wherein $R_8$ and $R_9$ have their previous significance; with (B) an organodithiophosphate having the formula:

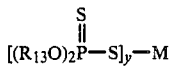

$$[(R_{13}O)_2\overset{\overset{S}{\|}}{P}-S]_y-M \qquad III$$

in which $R_{13}$ is a $C_1$-$C_{20}$ alkyl, $C_7$-$C_{18}$ alkyl phenyl or $C_7$-$C_{13}$ aralkyl group, M is a metal ion of Group IA, IB, IIA, IIB, VB, VIB, VIIB or VIII of the Periodic System of Elements, and y is the valency of M.

When any of the groups $R_7$, $R_8$, $R_9$, $R_{10}$, $R_{11}$, $R_{12}$ and $R_{13}$, independently, is a $C_1$-$C_{20}$ alkyl group, it may be of straight- or branched chain e.g. methyl, ethyl, n-propyl, iso-propyl, n-butyl, sec-butyl, n-pentyl, n-hexyl, n-heptyl, n-octyl, 2-ethylhexyl, n-nonyl, n-decyl, n-dodecyl, n-tetradecyl, n-hexadecyl, n-octadecyl or n-eicosyl.

When the group $R_8$ and/or $R_9$ is a $C_3$-$C_{20}$ alkenyl group, it may be of straight- or branched chain e.g. prop-2-enyl, but-2-enyl, 2-methyl-prop-2-enyl, pent-2-enyl, hexa-2,4-dienyl, dec-10-enyl or eicos-2-enyl.

$C_5$-$C_{12}$ cycloalkyl groups $R_8$ and/or $R_9$ may be cyclopentyl, cyclohexyl, cyclooctyl, cyclodecyl, adamantyl or cyclododecyl.

$C_7$-$C_{13}$ aralkyl groups $R_8$ and/or $R_9$ and/or $R_{13}$ are e.g. benzyl, 2-phenylethyl, benzhydryl or naphthylmethyl.

$C_6$-$C_{10}$ aryl groups $R_8$ and/or $R_9$ and/or $R_{10}$ are e.g. phenyl or naphthyl.

$C_7$-$C_{18}$ alkyl phenyl groups $R_{10}$ and/or $R_{13}$ are e.g. tolyl, xylyl, 4-isopropylphenyl, 4-tert. butylphenyl, 4-octylphenyl or 4-dodecylphenyl.

When $R_8$ and $R_9$, together with the nitrogen atom to which they are attached form a heterocyclic residue, this residue may be a morpholine, pyrrolidine, piperidine or perhydroazepine residue.

$C_1$-$C_{12}$ Alkylene moieties in the residue of formula II may be methylene, ethylene, 1:2- or 1:3-propylene, 1:4-butylene, 1:6-hexylene, 1:8-octylene, 1:10-decylene or 1:12-dodecylene.

Cations M include ammonium, sodium, potassium, calcium, magnesium, chromium, iron, nickel, cobalt and, especially, zinc.

Preferred reaction products according to the invention are those derived from compounds of formula IA in which $R_7$ is hydrogen or methyl and $R_8$ and $R_9$ are each a $C_1$-$C_{20}$ alkyl group, preferably a $C_4$-$C_{13}$ alkyl group, most preferably a $C_8$ alkyl group. Other preferred reaction products of the invention are those derived from compounds of formula IB in which $R_{10}$ and $R_{11}$ are simultaneously hydrogen or $R_{10}$ is hydrogen and $R_{11}$ is —$CH_2R_8R_9$ in which $R_8$ and $R_9$ are each $C_1$-$C_{20}$ alkyl, preferably $C_4$-$C_{13}$ alkyl, especially a $C_8$ alkyl group.

Specific preferred reactants (A) for producing the reaction products of the invention include:

1-(Dimethylaminomethyl)benzotriazole
1-(Diethylaminomethyl)benzotriazole
1-(Diisopropylaminomethyl)benzotriazole
1-(Di-n-hexylaminomethyl)benzotriazole
1-(Di-n-octylaminomethyl)benzotriazole
1-(Di-n-decylaminomethyl)benzotriazole
1-(Di-n-dodecylaminomethyl)benzotriazole
1-(Di-n-octadecylaminomethyl)benzotriazole
1-(Di-n-eicosylaminomethyl)benzotriazole
1-(Di-(prop-2-enyl)aminomethyl]benzotriazole
1-[Di-(but-2-enyl)aminomethyl]benzotriazole
1-[Di-(eicos-2-enyl)aminomethyl]benzotriazole
1-(Di-cyclohexylaminomethyl)benzotriazole
1-(Di-benzylaminomethyl)benzotriazole
1-(Di-phenylaminomethyl)benzotriazole
1-(4-morpholinomethyl)benzotriazole
1-(4-pyrrolidinomethyl)benzotriazole
1-(4-piperidinomethyl)benzotriazole
1-(4-perhydroazepinomethyl)benzotriazole
1-(Dibutoxypropyl-aminomethyl)benzotriazole
1-(Dibutylthiopropyl-aminomethyl)benzotriazole
1-(Dibutylaminopropyl-aminomethyl)benzotriazole
1,2,4-Triazole
1-(or 4)-(Dimethylaminomethyl)-1,2,4-triazole
1-(or 4)-)Diethylaminomethyl)-1,2,4-triazole
1-(or 4)-(Di-isopropylaminomethyl)-1,2,4-triazole
1-(or 4)-(Di-n-butylaminomethyl)-1,2,4-triazole
1-(or 4)-(Di-n-hexylaminomethyl)-1,2,4-triazole
1-(or 4)-(Di-n-octylaminomethyl)-1,2,4-triazole
1-(or 4)-(Di-n-decylaminomethyl)-1,2,4-triazole
1-(or 4)-(Di-n-dodecylaminomethyl)-1,2,4-triazole
1-(or 4)-(Di-n-octadecylaminomethyl)-1,2,4-triazole
1-(or 4)-(Di-n-eicosylaminomethyl)-1,2,4-triazole
1-(or 4)-[Di-(prop-2-enyl)aminomethyl]-1,2,4-triazole
1-(or 4)-[Di-(but-2-enyl)aminomethyl]-1,2,4-triazole
1-(or 4)-[Di-(eicos-2-enyl)aminomethyl]-1,2,4-triazole
1-(or 4)-(Di-cyclohexylaminomethyl)-1,2,4-triazole
1-(or 4)-(Di-benzylaminomethyl)-1,2,4-triazole
1-(or 4)-(Di-phenylaminomethyl)-1,2,4-triazole
1-(or 4)-(4-morpholinomethyl)-1,2,4-triazole
1-(or 4)-(4-pyrrolidinomethyl)-1,2,4-triazole
1-(or 4)-(4-piperidinomethyl)-1,2,4-triazole
1-(or 4)-(4-perhydroazepinomethyl)-1,2,4-triazole
1-(or 4)-(Dibutoxypropyl-aminomethyl)-1,2,4-triazole
1-(or 4)-(Dibutylthiopropyl-aminomethyl)-1,2,4-triazole
1-(or 4)-(Di-butylaminopropyl-aminomethyl)-1,2,4-triazole Specific preferred reactants (B) for producing the reaction products of the invention include:
zinc bis[(O,O'-di-methyl)dithiophosphate],
zinc bis[(O,O'-di-ethyl)dithiophosphate]
zinc bis[(O,O'-di-n-propyl)dithiophosphate],
zinc bis[(O,O'-di-isobutyl)dithiophosphate]
zinc bis[(O,O'-di-dimethylbutyl)dithiophosphate],
zinc bis[(O,O'-di-n-pentyl)dithiophosphate]
zinc bis[(O,O'-di-n-hexyl)dithiophosphate],
zinc bis[(O,O'-di-n-eicosyl)dithiophosphate]
zinc bis[(O,O'-di-1,3-dimethylbutylphenyl)dithiophosphate],
zinc bis[(O,O'-dodecylphenyl)dithiophosphate] more preferably.
zinc bis[(O,O'-di-2-ethylhexyl)dithiophosphate],
zinc bis[(O,O'-di-p-nonylphenyl)dithiophosphate] and mixtures of
zinc bis(isobutyl)- and zinc bis(hexyl)dithiophosphate The reaction between components (A) and (B) may be effected at temperatures ranging from 30° to 150° C., preferably from 50° to 110° C. The reaction is desirably continued until the reaction mixtures become clear. A reaction time ranging from 20 minutes to three hours is normally adequate for this purpose. The reactants (A) and (B) may be reacted in approximately stoichiometric proportions or either may be used in excess.

The compounds of formula IA are known compounds and may be produced by reacting an optionally alkyl-substituted benzotriazole of formula:

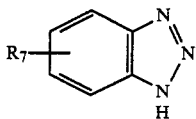

wherein $R_7$ has its previous significance, with formaldehyde and with an amine of formula $$HNR_8R_9 \quad\quad V$$

wherein $R_8$ and $R_9$ have their previous significance.

Some of the compounds of formula IB are new compounds, which are the subject of a separate patent application GB No. 2156813, while others, are known compounds.

Each of the compounds of formula IB, apart from the parent compound 1,2,4-triazole itself, may be produced by reacting an optionally substituted 1,2,4-triazole having the formula:

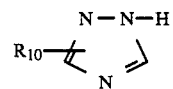

wherein $R_{10}$ has its previous significance other than hydrogen, with an N-$C_1$-$C_{12}$ alkylating agent capable of introducing a $C_1$-$C_{12}$ alkyl group $R_{11}$.

The reactants (B) are known, and many are commercially-available.

The new reaction products have improved solubility in functional fluids and have valuable properties as metal deactivators and as antioxidants in functional fluids.

Accordingly, the present invention also provides a composition comprising a functional fluid, and as metal deactivator, especially for copper, a metal deactivating proportion, preferably 0.001% to 5% by weight, based on total composition, of a reaction product according to the invention. Examples of functional fluids useful as substrates for the compositions of the invention are lubricants having a mineral oil, poly-alpha olefin or synthetic carboxylic ester base; hydraulic fluids based on mineral oils, phosphate esters, metal-working fluids having, as their base, mineral oil systems; and transformer and switch oils.

Examples of synthetic lubricants include lubricants based on a diester of a dibasic acid and a monohydric alcohol, for instance dioctyl sebacate or dinonyl adipate; on a triester of trimethylol propane and a monobasic acid or mixture of such acids, for instance trimethylol propane tripelargonate, trimethylol propane tricaprylate or mixtures thereof; on a tetraester of pentaerythritol and a monobasic acid or mixture of such acids, for instance pentaerythritol tetracaprylate; or on complex esters derived from monobasic acids, dibasic acids and polyhydric alcohols, for instance a complex ester derived from trimethylol propane, caprylic acid and sebacic acid; or of mixtures thereof.

Other synthetic lubricants are those known to the art-skilled and described e.g. in "Schmiermittel-Taschenbuch" (Huethig Verlag, Heidelberg 1974). Especially suitable, apart from the preferred mineral oils are e.g. phosphates, glycols, polyglycols, polyalkylene glycols and poly-alpha olefins.

For use in oil-based functional fluids, reaction products of the invention are preferred which are derived from reactants IA or IB in which $R_8$ and/or $R_9$ is an oleophilic group.

In order to improve various applicational properties, the compositions of the invention may also contain other additives such as, for oil-based systems, one or more of antioxidants, other metal deactivators, rust inhibitors, viscosity-index improvers, pour-point depressants, dispersants/surfactants or anti-wear additives; and for aqueous-based systems, one or more of antioxidants, corrosion- and rust inhibitors, further metal deactivators, extreme pressure- or anti-wear additives, complexing agents, precipitation inhibitors, biocides, buffering agents and anti-foams.

For oil-based systems, examples of other additives are:

EXAMPLES OF PHENOLIC ANTIOXIDANTS

1. Alkylated Monophenols
2,6-di-tert.-butylphenol
2-tert.-butyl-4,6-dimethylphenol
2,6-Di-tert.-butyl-4-ethylphenol
2,6-Di-tert.-butyl-4-n-butylphenol
2,6-Di-tert.-butyl-4-i-butylphenol
2,6-Di-cyclopentyl-4-methylphenol
2-(α-Methylcyclohexyl)-4,6-dimethylphenol
2,6-Di-octadecyl-4-methylphenol
2,4,6-Tri-cyclohexylphenol
2,6-Di-tert.-butyl-4-methoxymethylphenol 2. Alkylated Hydroquinones
2,6-Di-tert.-butyl-4-methoxyphenol
2,5-Di-tert.-butyl-hydroquinone
2,5-Di-tert.-amyl-hydroquinone
2,6-diphenyl-4-octadecyloxyphenol 3. Hydroxylated Thiodiphenylethers
2,2'-Thio-bis(6-tert.-butyl-4-methylphenol)
2,2'-Thio-bis-(4-octylphenol)
4,4'-Thio-bis-(6-tert.-butyl-3-methylphenol)
4,4'-Thio-bis-(6-tert.-butyl-2-methylphenol)

4. Alkylidene-Bisphenols
2,2'-Methylene-bis-(6-tert.-butyl-4-methylphenol)
2,2'-Methylene-bis-(6-tert.-butyl-4-ethylphenol)
2,2'-Methylene-bis-[4-methyl-6-(αmethylcyclohexyl)-phenol]
2,2'-Methylene-bis-(4-methyl-6-cyclohexylphenol)
2,2'-Methylene-bis-(6-nonyl-4-methylphenol)
2,2'-Methylene-bis-(4,6-di-tert.-butylphenol)
2,2'-Ethylidene-bis-(4,6-di-tert.-butylphenol)
2,2'-Ethylidene-bis-(6-tert.-butyl-4-isobutyphenol)
2,2'-Methylene-bis-[6-(αmethylbenzyl)-4-nonylphenol]
2,2'Methylene-bis-[6-(α,α-dimethylbenzyl)-4-nonylphenol]
4,4'-Methylene-bis-(6-tert.-butyl-2-methylphenol)
1,1-Bis-(5-tert.-butyl-4-hydroxy-2-methylphenol)-butane
2,6-Di-(3-tert.-butyl-5-methyl-2-hydroxybenzyl)-4-methylphenol
1,1,3-Tris-(5-tert.-butyl-4-hydroxy-2-methylphenyl)-3-n-dodecylmercaptobutane
Ethyleneglycol-bis-[3,3-bis-(3'-tert.-butyl-4'-hydroxyphenyl)butyrate]
Di-(3-tert.-butyl-4-hydroxy-5-methylphenyl)-dicyclopentadiene
Di-[3'-tert.-butyl-2'-hydroxy-5'-methyl-benzyl)-6-tert.-butyl-4-methyl-phenyl]-terephthalate 5. Benzyl Compounds
1,3,5-Tri-(3,5-di-tert.-butyl-4-hydroxybenzyl)-2,4,6-trimethylbenzene Di-(3,5-di-tert.-butyl-4-hydroxybenzyl)-sulfide
Bis-(4-tert.-butyl-3-hydroxy-2,6-dimethylbenzyl)dithiolterephthalate
1,3,5-Tris-(3,5-di-tert.-butyl-4-hydroxybenzyl)-isocyanurate
1,3,5-Tris-(4-tert.-butyl-3-hydroxy-2,6-dimethylbenzyl)isocyanurate
3,5-Di-tert.-butyl-4-hydroxybenzyl-phosphonic acid-dioctadecylester
3,5-Di-tert.-butyl-4-hydroxybenzyl-phosphonic acid-monoethylester Calcium-salt 6. Acylaminophenols
4-Hydroxy-lauric acid anilide
4-Hydroxy-stearic acid anilide
2,4-Bis-octylmercapto-6-(3,5-di-tert.-butyl-4-hydroxyanilino)-s-triazine
N-(3,5-di-tert.-butyl-4-hydroxyphenyl)-carbamic acid octyl ester 7. Esters of β-(3,5-Di-tert.-butyl-4-hydroxyphenyl)-propionic acid
with mono- or polyhydric alcohols e.g. with

| Methanol | Diethyleneglycol |
| Octadecanol | Triethyleneglycol |
| 1,6-Hexanediol | Pentaerythritol |
| Neopentylglycol | Tris-hydroxyethyl-isocyanurate |
| Thiodiethyleneglycol | Di-hydroxyethyl-oxalic acid diamide |

8. Esters of β-(5-tert.-butyl-4-hydroxy-3-methylphenyl)-propionic acid
with mono- or polyhydric alcohols e.g. with

| Methanol | Diethyleneglycol |
| Octadecanol | Triethyleneglycol |
| 1,6-Hexanediol | Pentaerythritol |
| Neopentylglycol | Tris-hydroxyethyl-osocyanurate |
| Thiodiethyleneglycol | Di-hydroxyethyl-oxalic acid diamide |

9. Amides of β-(3,5-Di-tert.-butyl-4-hydroxyphenyl)-propionic acid e.g.
N,N'-Di-(3,5-di-tert.-butyl-4-hydroxyphenylpropionyl)hexamethylene-diamine
N,N'-Di-(3,5-di-tert.-butyl-4-hydroxyphenylpropionyl)trimethylene-diamine
N,N'-Di-(3,5-di-tert.-butyl-4-hydroxyphenylpropionyl)-hydrazine

EXAMPLES OF AMINE ANTIOXIDANTS

N,N'-Di-isopropyl-p-phenylenediamine
N,N'-Di-sec.-butyl-p-phenylenediamine
N,N'-Bis(1,4-dimethyl-pentyl)-p-phenylenediamine
N,N'-Bis(1-ethyl-3-methyl-pentyl)-p-phenylenediamine
N,N'-Bis(1-methyl-heptyl)-p-phenylenediamine
N,N'-Dicyclohexyl-p-phenylenediamine
N,N'-Diphenyl-p-phenylenediamine
N,N'-Di-(naphthyl-2-)-p-phenylenediamine
N-Isopropyl-N'-phenyl-p-phenylenediamine
N-(1,3-dimethyl-butyl)-N'-phenyl-p-phenylenediamine
N-(1-Methyl-heptyl)-N'-phenyl-p-phenylenediamine
N-Cyclohexyl-N'-phenyl-p-phenylenediamine
4-(p-Toluol-sulfonamido)-diphenylamine
N,N'-dimethyl-N,N'-di-sec.-butyl-p-phenylenediamine
Diphenylamine
4-Isopropoxy-diphenylamine
N-Phenyl-1-naphthylamine
N-Phenyl-2-naphthylamine
octylated Diphenylamine
octylated N-phenyl-α(or β)naphthylamine
4-n-Butylaminophenol
4-Butyrylamino-phenol
4-Nonanoylamino-phenol
4-Iodecanoylamino-phenol
4-Octadecanoylamino-phenol
Di-(4-methoxy-phenyl)-amine
2,6-Di-tert.-butyl-4-dimethylamino-methyl-phenol
2,4'-diamino-diphenylmethane
4,4'-Diamino-diphenylmethane
N,N,N',N'-Tetramethyl-4,4'-diamino-diphenylmethane
1,2-Di-(phenylamino)-ethane
1,2-Di-[(2-methyl-phenyl)-amino]-ethane
1,3-Di-(phenylamino)-propane
(o-tolyl)-biguanide
Di-[4-(1',3'-dimethyl-butyl)-phenyl]amine

EXAMPLES OF METAL PASSIVATORS ARE for copper e.g.
Benzotriazole, tolutriazole and derivatives thereof, Tetrahydrobenzotriazole, 2-mercaptobenzthiazole, 2,5-dimercaptothiadiazole, salicylidene-propylenediamine and salts of salicylaminoguanidine.

EXAMPLES OF RUST INHIBITORS ARE (a) Organic acids, their esters, metal salts and anhydrides e.g. N-oleoyl-sarcosine, sorbitan-mono-oleate, lead-naphthenate, dodecenyl-succinic acid (and its partial esters and amides), 4-nonyl-phenoxy-acetic acid.
(b) nitrogen-containing compounds e.g.
  I. Primary, secondary or tertiary aliphatic or cycloaliphatic amines and amine-salts of organic and inorganic acids e.g. oil-soluble alkylammonium carboxylates
  II. Heterocyclic compounds e.g substituted imidazolines and oxazolines
(c) Phosphorus-containing compounds e.g.
  Amine salts of phosphonic acid partial esters, zinc dialkyldithio phosphates
(d) Sulfur-containing compounds e.g.
  Barium-dinonylnaphthalene-n-sulfonates, calcium petroleum sulfonates

EXAMPLES OF VISCOSITY-INDEX IMPROVERS ARE E.G.

Polymethacrylates, vinylpyrrolidone/methacrylate-copolymers, polybutenes, olefin-copolymers, styrene/acrylate-copolymers.

EXAMPLES OF POUR-POINT DEPRESSANTS ARE E.G.

Polymethacrylates, or alkylated naphthalene derivatives

EXAMPLES OF DISPERSANTS/SURFACTANTS ARE E.G.

Polybutenylsuccinic acid-amides, polybutenylphosphonic acid derivatives, basic magnesium-, calcium-, and bariumsulfonates and -phenolates.

EXAMPLES OF ANTI-WEAR ADDITIVES ARE E.G.

Sulfur- and/or phosphorus- and/or halogen-containing compounds e.g. sulfurised vegetable oils, zinc dialkyldithiophosphates, tritolyl-phosphate, chlorinated paraffins, alkyl- and aryldisulfides.

The new reaction products of the invention combine excellent metal deactivation properties with good solubility in oil-based functional fluids.

The following Examples further illustrate the present invention. All parts and percentages given therein are by weight.

EXAMPLE 1

A mixture of 69 grams of 1,2,4-triazole and 771 grams of zinc bis[(O,O'-di-2-ethylhexyl)dithiophosphate] is gradually heated to a temperature of 95° C. with stirring. After the resulting mixture has been stirred at the temperature for a period of two hours, the resulting reaction produced is clear and the reaction was discontinued at this stage. Stirring is continued whilst the product cools to room temperature. The final product is a clear yellow viscous oil.

EXAMPLE 2

A mixture of 322 g 1-(di-2-ethylhexylaminomethyl)-1,2,4-triazole and 771 grams of zinc bis[(O,O'-di-2-ethylhexyl) dithiophosphate] is gradually heated to a temperature of 95° C. with stirring. After the resulting mixture has been stirred at this temperature for a period of 30 minutes the resulting reaction product is clear and the reaction is discontinued at this stage. Stirring is continued whilst the product cools to room temperature. The final product is a clear yellow oil.

EXAMPLES 3 AND 4

A 0.05% solution of the product of Example 1 or 2 is prepared in a turbine quality mineral oil containing 50 ppm of added, dissolved sulphur.

A copper strip (60×10×1 mm) is polished with 100 grade silicon carbide grit which has been picked up on cotton wool wetted with petroleum ether. The polished strip is then immediately totally immersed in the prepared solution which is maintained at 100° C. for 2 hours. After this time, the strip is removed, washed with petroleum ether, dried and its colour is compared with those of the ASTM D130 Copper Strip Corrosion Standard Chart. On this rating, 1 represents zero to slight tarnish; 2 represents moderate tarnish; 3 represents dark tarnish; and 4 represents corrosion; the designations A, B and D indicate shadings within the numerical gradings.

The results are set out in the following Table I:

1,2,4-Triazole did not have the required solubility (0.05%) in the mineral oil in order for it to be submitted to this test.

EXAMPLES 5 AND 6

Turbine Oil Stability Test (TOST)—modified ASTM D943

300 mls of a test oil comprising 99.70% by weight of a petroleum-based oil, 0.25% by weight of the product of Example 1 or 2 and 0.05% by weight of partially-esterified dodecenyl succinic acid is heated to 95° C. in the presence of 60 mls of water, oxygen at a flow rate of 3±0.5 liters/hour and an iron-copper catalyst. After 500 hours, the oxidised oil is filtered through a 10 micron filter paper to determine the amount of sludge formed during the test.

The results are summarised in Table II:

TABLE II

| Example | Antioxidant | Sludge formed (mg) |
|---|---|---|
| — | — | >5000 |
| 5 | product of Example 1 | 88 |
| 6 | product of Example 2 | 108 |

EXAMPLES 7 TO 14

Using the procedure described in Example 1, further reaction products according to the invention were produced by reacting specific compounds having the formula IB:

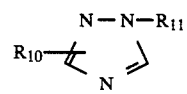

with various compounds of formula III:

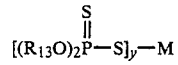

The reaction products so obtained were then evaluated in the copper strip test (using the procedure described in Examples 3 and 4) and in the turbine oil stability test (TOST) (see Examples 5 and 6).

The results are summarised in Table III:

TABLE III

| Example | $R_{10}$ | $R_{11}$ | $R_{13}$ | y | M | Metal Appearance | Sludge (mg) |
|---|---|---|---|---|---|---|---|
| — | | | no additive | | | 3B | >5000 |
| 7 | $CH_3$ | H | $C_4H_9CH(C_2H_5)CH_2-$ | 2 | Zn | 1A | 84 |
| 8 | $C_2H_5$ | H | $C_4H_9CH(C_2H_5)CH_2-$ | 2 | Zn | 1A | 213 |
| 9 | $n-C_4H_9$ | H | $C_4H_9CH(C_2H_5)CH_2-$ | 2 | Zn | 1A | 298 |
| 10 | $i-C_4H_9$ | H | $C_4H_9CH(C_2H_5)CH_2-$ | 2 | Zn | 1A | 39 |
| 11 | $n-C_6H_{13}$ | H | $C_4H_9CH(C_2H_5)CH_2-$ | 2 | Zn | 1B | 270 |
| 12 | cyclohexyl | H | $C_4H_9CH(C_2H_5)CH_2-$ | 2 | Zn | 1A | 126 |
| 13 | benzyl | H | $C_4H_9CH(C_2H_5)CH_2-$ | 2 | Zn | 1A | 98 |
| 14 | phenyl | H | $C_4H_9CH(C_2H_5)CH_2-$ | 2 | Zn | 1B | 88 |

TABLE I

| Example | Deactivator | Metal Appearance | Solubility % |
|---|---|---|---|
| — | none | magenta - rating 3B | — |
| — | 1,2,4-triazole | — | <0.05 |
| 3 | product of Example 1 | no change - rating 1A | >10 |
| 4 | product of Example 2 | no change - rating 1A | >1 |

EXAMPLE 15

Using the procedure described in Example 1, 1-[di-(2-ethylhexyl)aminomethyl]-methylbenzotriazole is reacted with zinc bis[(O,O'-di-2-ethylhexyl)dithiophosphate].

The reaction product so obtained gave a copper strip rating (see Examples 3 and 4) of 1A and a sludge value in the turbine oil stability test (TOST)—see Examples 5 and 6—of 99 mg.

What is claimed is:

1. Reaction product obtained by reacting, at elevated temperature,
(A) a triazole having the formula IA or IB:

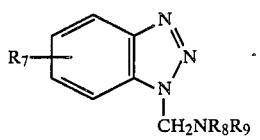

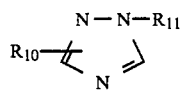

wherein $R_7$ is hydrogen or a $C_1$–$C_{20}$ alkyl residue;
$R_8$ and $R_9$ are the same or different and each is $C_1$–$C_{20}$ alkyl, $C_3$–$C_{20}$ alkenyl, $C_5$–$C_{12}$ cycloalkyl, $C_7$–$C_{13}$ aralkyl, $C_6$–$C_{10}$ aryl or $R_8$ and $R_9$, together with the nitrogen atom to which they are attached, form a 5-, 6- or 7-membered heterocyclic residue or $R_8$ and $R_9$ is each a residue of formula:

wherein
X is O, S or $N(R_{12})$, $R_{12}$ is hydrogen or $C_1$–$C_{20}$ alkyl, "alkylene" is a $C_1$–$C_{12}$ alkylene residue and n is 0 or an integer from 1 to 6;
$R_{10}$ is hydrogen, $C_1$–$C_{20}$ alkyl or $C_6$–$C_{10}$ aryl or $C_7$–$C_{18}$ alkyl phenyl; and $R_{11}$ is hydrogen, $C_1$–$C_{20}$ alkyl or a residue —$CH_2NR_8R_9$ wherein $R_8$ and $R_9$ have their previous significance; with
(B) an organodithiophosphate having the formula:

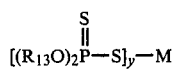

in which $R_{13}$ is a $C_1$–$C_{20}$ alkyl, $C_7$–$C_{18}$ alkyl phenyl or $C_7$–$C_{13}$ aralkyl group, M is a metal ion of Group IA, IB, IIA, IIB, VB, VIB, VIIB or VIII of the Periodic System of Elements, and y is the valency of M.

2. Reaction product according to claim 1 wherein reactant (A) is a compound of formula IA in which $R_7$ is hydrogen or methyl and $R_8$ and $R_9$ are each a $C_1$–$C_{20}$ alkyl group.

3. Reaction product according to claim 2 wherein $R_8$ and $R_9$ are each a $C_4$–$C_{13}$ alkyl group.

4. Reaction product according to claim 3 wherein $R_8$ and $R_9$ are each a $C_8$ alkyl group.

5. Reaction product according to claim 1 wherein the reactant (A) is a compound of formula IB in which $R_{10}$ and $R_{11}$ are simultaneously hydrogen or $R_{10}$ is hydrogen and $R_{11}$ is —$CH_2R_8R_9$ in which $R_8$ and $R_9$ are each $C_1$–$C_{20}$ alkyl.

6. Reaction product according to claim 5 wherein $R_8$ and $R_9$ are each a $C_4$–$C_{13}$ alkyl group.

7. Reaction product according to claim 6 wherein $R_8$ and $R_9$ are each a $C_8$ alkyl group.

8. Reaction product according to claim 1 wherein reactant (B) is zinc bis[(O,O'-di-2-ethylhexyl)dithiophosphate].

9. Reaction product according to claim 1 wherein the reaction between components (A) and (B) is effected at a temperature ranging from 30° to 150° C.

10. Reaction product according to claim 9 wherein the reaction temperature ranges from 50° to 110° C.

11. Reaction product according to claim 1 wherein the reaction is effected until the reaction mixture becomes clear.

12. Reaction product according to claim 1 wherein reactant (A) is 1,2,4-triazole or 1-(di-2-ethylhexylaminomethyl)-1,2,4-triazole and reactant (B) is zinc bis[(O,O'-di-2-ethylhexyl)dithiophosphate].

* * * * *